US008277838B2

(12) United States Patent
Nguyen

(10) Patent No.: US 8,277,838 B2
(45) Date of Patent: Oct. 2, 2012

(54) TRANSDERMAL DELIVERY OF DRUGS BASED ON CRYSTAL SIZE

(75) Inventor: Viet Nguyen, Miami, FL (US)

(73) Assignee: Noven Pharmaceuticals, Inc., Miami, FL (US)

( * ) Notice: Subject to any disclaimer, the term of this patent is extended or adjusted under 35 U.S.C. 154(b) by 0 days.

(21) Appl. No.: 12/979,978

(22) Filed: Dec. 28, 2010

(65) Prior Publication Data

US 2011/0091511 A1    Apr. 21, 2011

Related U.S. Application Data

(62) Division of application No. 11/245,106, filed on Oct. 7, 2005.

(60) Provisional application No. 60/617,561, filed on Oct. 8, 2004.

(51) Int. Cl.
A61F 13/02     (2006.01)
A61F 13/00     (2006.01)
A61L 15/16     (2006.01)
A61K 9/70      (2006.01)

(52) U.S. Cl. .................. 424/448; 424/449; 424/443
(58) Field of Classification Search .............. 424/448, 424/449, 443
See application file for complete search history.

(56) References Cited

U.S. PATENT DOCUMENTS

| | | |
|---|---|---|
| 4,390,520 A | 6/1983 | Nagai et al. |
| 4,559,222 A | 12/1985 | Enscore et al. |
| 4,584,355 A | 4/1986 | Blizzard et al. |
| 4,585,836 A | 4/1986 | Homan et al. |
| 4,591,622 A | 5/1986 | Blizzard et al. |
| 4,655,767 A | 4/1987 | Woodard et al. |
| 4,994,267 A | 2/1991 | Sabalotsky |
| 4,994,278 A | 2/1991 | Sablotsky et al. |
| 5,446,070 A | 8/1995 | Mantelle |
| 5,474,783 A | 12/1995 | Miranda et al. |
| 5,474,787 A | 12/1995 | Grey et al. |
| 5,656,286 A | 8/1997 | Miranda et al. |
| 5,762,952 A | 6/1998 | Bamhart et al. |
| 5,958,446 A | 9/1999 | Miranda et al. |
| 6,024,976 A | 2/2000 | Miranda et al. |
| 6,221,383 B1 | 4/2001 | Miranda et al. |

(Continued)

FOREIGN PATENT DOCUMENTS

WO    WO 0041538 A2 *   7/2000

OTHER PUBLICATIONS

Kurnik et al. "Modeling of diffusion and crystal dissolution in controlled release systems", Journal of controlled Release 45 (1997), 257-264.*

(Continued)

Primary Examiner — Isis Ghali
(74) Attorney, Agent, or Firm — Foley & Lardner LLP

(57) ABSTRACT

A blend of at least two polymers in combination with a drug provides a pressure-sensitive adhesive composition for a transdermal drug delivery system in which the drug is delivered from the pressure-sensitive adhesive composition and through dermis when the pressure-sensitive adhesive composition is in contact with human skin. According to the invention, providing drug having differing crystal sizes as well as drug which is solublized in the pressure-sensitive adhesive composition controls the rate of drug delivery from the pressure-sensitive adhesive composition.

23 Claims, 2 Drawing Sheets

U.S. PATENT DOCUMENTS

| | | | |
|---|---|---|---|
| 6,235,306 | B1 | 5/2001 | Miranda et al. |
| 6,562,363 | B1 | 5/2003 | Mantelle et al. |
| 2001/0033858 | A1* | 10/2001 | Zhang .......................... 424/443 |
| 2003/0137067 | A1 | 7/2003 | Cooper et al. |
| 2005/0013852 | A1 | 1/2005 | Lee et al. |
| 2005/0069591 | A1 | 3/2005 | Bernstein et al. |

OTHER PUBLICATIONS

Nitto Denko "Advancing Drug delivery Technologies", Mar. 29, 2004.*

Vaughan, "Using Solubility Parameters in Cosmetics Formulation," *J. Soc. Cosmet. Chem.*, vol. 36, pp. 319-333, 1985.

Sobieski et al., "Silicone Pressure Sensitive Adhesives," *Handbook of Pressure-Sensitive Adhesive Technology*, $2^{nd}$ ed., pp. 508-517 (D. Satas, ed.), 1989.

Satas, ed., "Acrylic Adhesives," *Handbook of Pressure-Sensitive Adhesive Technology*, $2^{nd}$ ed., pp. 396-456, 1989.

Merck Index, $11^{th}$ ed., Merck & Co., Rahway, NJ, pp. ther-5 to ther-29, 1980.

International Preliminary Report on Patentability, issued on Apr. 19, 2007 in application No. PCT/US05/35807).

International Search Report issued on Apr. 24, 2006 in application No. PCT/US05/35807.

Office Action issued on Jun. 9, 2010 by the Examiner in U.S. Appl. No. 11/245,106 (US 2006/0078603).

Office Action issued on Dec. 28, 2009 by the Examiner in U.S. Appl. No. 11/245,106 (US 2006/0078603).

Office Action issued on Jul. 8, 2009 by the Examiner in U.S. Appl. No. 11/245,106 (US 2006/0078603).

Office Action issued on Dec. 22, 2010 by the Examiner in U.S. Appl. No. 11/245,106 (US 2006/0078603).

Office Action issued on Jul. 12, 2011 by the Examiner in U.S. Appl. No. 11/245,106 (US 2006/0078603).

* cited by examiner

TRANSDERMAL DELIVERY OF DRUGS BASED ON CRYSTAL SIZE

This application claims the benefit of provisional application 60/617,561 filed Oct. 8, 2004, which is hereby incorporated by reference in its entirety.

FIELD OF THE INVENTION

This invention relates generally to transdermal drug delivery systems, and more particularly to pharmaceutically acceptable adhesive matrix compositions. The invention additionally relates to transdermal drug delivery systems providing substantially zero order drug release profiles for an extended period of time of up to seven days or longer.

BACKGROUND OF THE INVENTION

The use of transdermal drug delivery systems to topically administer an active agent is well known. These systems incorporate the active agent into a carrier composition, such as a polymeric and/or pressure-sensitive adhesive composition, from which the active agent is delivered through the skin or mucosa of the user.

Active-ingredient-containing transdermal drug delivery systems ("patches") are essentially divided into two major technical systems: reservoir systems and matrix systems. The present invention relates to matrix systems where the active ingredient(s) are embedded in a semi-solid matrix made up of a single polymer or a blend of polymers.

Both types of devices employ a backing layer that forms the protective outer surface of the finished transdermal system and which is exposed to the environment during use. A release liner or protective layer that forms the inner surface covers the polymeric adhesive which is employed for affixing the system to the skin or mucosa of a user. The release liner or protective layer is removed prior to application, exposing the adhesive, typically a pressure-sensitive adhesive.

In the "classic" reservoir-type device, the active agent is typically dissolved or dispersed in a carrier to yield a non-finite carrier form, such as, for example, a fluid or gel. In the reservoir-type device, the active agent is generally kept separate from the adhesive. The device has a pocket or "reservoir" which physically serves to hold the active agent and carrier, and which is formed in or by a backing layer. A peripheral adhesive layer is then used to affix the device to the user.

The reservoir-type devices have a number of disadvantages including a non-uniform drug release profile where a high dose of drug is initially released upon application to the user, often described as a "burst effect." This burst or high initial release of drug then drops off after a period of time to a rate that necessary to achieve a therapeutically effective amount. Drug delivery according to this profile is generally described as first order release.

While classic reservoir-type devices are still in use today, the term reservoir is being used interchangeably herein with matrix-type devices which still rely upon a separate adhesive means used to affix the device to the user.

In a matrix-type device, the active agent is dissolved or dispersed in a carrier that typically is in a finite carrier form. The carrier form can be self-adhesive or non-adhesive. Non-adhesive matrix-type devices, that is, those which still rely on a separate adhesive means to affix the device to the user, employ a drug permeable adhesive layer (often referred to as an "in-line adhesive" since the drug must pass through this layer) applied over the drug matrix carrier layer. To better control the release rate of the drug, the non-adhesive matrix-type devices often employ one or more additional drug permeable layers such as, for example, rate controlling membranes. The non-adhesive matrix-type devices often contain excipients, such as drug delivery enhancers, to help control the release rate. These devices are often referred to as multilayer or multilaminate.

In a "monolithic" or "monolayer" matrix-type device, the active agent is typically solubilized or homogenously blended in an adhesive carrier composition, typically a pressure-sensitive adhesive or bioadhesive, which functions as both the drug carrier and the means of affixing the system to the skin or mucosa. Such devices, commonly referred to as drug-in-adhesive devices, are described, for example, in U.S. Pat. Nos. 4,994,267; 5,446,070; 5,474,783 and 5,656,286, all of which are assigned to Noven Pharmaceuticals, Inc., Miami, Fla. and herein incorporated by reference.

While matrix-type devices, especially drug-in-adhesive devices, achieve more uniform and controlled drug deliver rates over longer periods of time, most transdermal systems remain subject to a higher initial drug release than is required to achieve therapeutic efficacy. For many drugs and/or therapeutic situations, it would be advantageous to eliminate or suppress this higher initial release and achieve a "steady state" (zero order) release profile which uniformly delivers a therapeutically effective amount of drug over the extended duration of device's desired use, preferably up to 7 days or more.

The high initial blood level concentration of certain drugs may cause adverse or undesired effects, or create toxicity concerns, thereby limiting the use of transdermal administration. In other instances, the higher initial blood level concentration may reduce the amount of drug required for treatment to the point of risking under dosing, or the higher initial blood level concentration may make it impractical to increase the duration of the device's application while retaining therapeutic effectiveness. Reducing the frequency of replacing the transdermal drug delivery system would increase user compliance, reduce any lag or drop off in efficacious blood levels, and reduce the amount of drug required for treatment (also provided by reducing the higher initial blood level associated with the higher release rate).

Drug concentration in transdermal delivery systems can vary widely depending on the drug and polymers used. Low drug concentrations in the adhesive can result in difficulties in achieving an acceptable delivery rate of the medicament, preferably one approximating zero order kinetics. High drug concentrations, on the other hand, frequently affect the adhesion properties of the adhesives, and tend to promote unwanted crystallization and "burst effect" (i.e., rapid drug release).

Simple diffusion models for permeation of drugs through the skin suggest that permeation rates are concentration dependent, that is, dependent on both the amount and the degree of drug within the pressure-sensitive adhesive composition. Some adhesives, such as, for example, polyacrylate adhesives have a high affinity for many drugs and thus tend to solubilize higher concentrations of drug than do, for example, rubber adhesives. However, the use of polyacylates alone as the adhesive is not without its drawbacks as polyacrylate adhesives, for example, may tend to cause skin irritation, especially when the transdermal device is used for extended periods of time.

Various transdermal drug delivery systems have been described in the literature. For example, U.S. Pat. No. 4,559,222 describes a multi-layer non-adhesive matrix-type device having a reservoir layer which comprises mineral oil, colloidal silicon dioxide, a polyisobutylene adhesive and a drug, which may be clonidine, at a concentration greater than saturation. The system includes a drug release rate controlling layer through which the drug may diffuse at a known rate, an adhesive layer, which may also contain a loading of drug, and a protective strippable coating.

U.S. Pat. No. 5,762,952 describes a system comprising a self-crosslinking acrylate adhesive into which a drug, such as clonidine, is incorporated together with auxiliaries, such as solvents or absorption promoters, that are volatile at relatively high temperatures. The patent discusses that the crosslinked acrylate adhesive is important to increase the consistency of the adhesive substance and to incorporate either a large amount of the active drug or a large amount of an inactive solubilizing agent into the adhesive.

Therefore, despite the existence of many different types of transdermal delivery systems in the art, there remains a continuing need for improving the release profile of drugs to achieve substantially zero order, as well as extending the duration of use of each individual transdermal drug delivery system.

SUMMARY OF THE INVENTION

Figure 1:
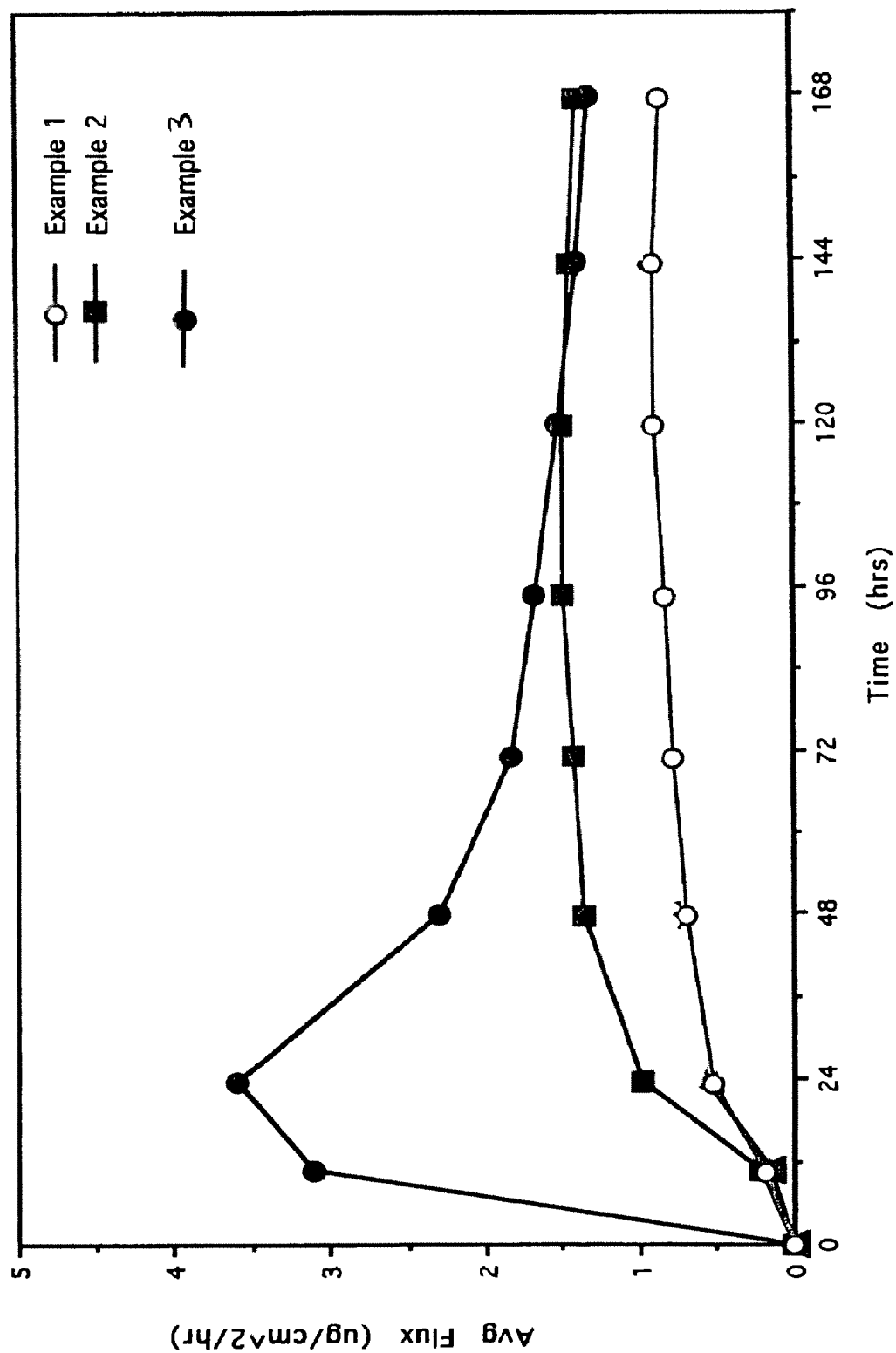
FIG. 1 is a graphic representation of the effects on drug delivery, onset and profile of clonidine with different crystal sizes of the drug in pressure-sensitive adhesive compositions.

Based upon the foregoing, it is an object of the present invention to overcome the limitations of the prior transdermal systems, and to provide a transdermal drug delivery system which allows modulation of drug permeation and delivery rates and profiles.

Another object is to provide a transdermal system, which is simple and inexpensive to manufacture. The present invention provides a transdermal drug delivery system for the topical application of one or more active agents contained in one or more polymeric and/or adhesive carrier layers which is manufactured to optimize drug loading while providing desirable adhesion to skin or mucosa as well as providing modulation of the drug delivery and profile.

The invention is also directed to compositions and methods of controlling drug delivery rates, onset and profiles of at least one active agent in a transdermal delivery system by selectively incorporating in the transdermal drug delivery systems drugs in certain crystallize size, alone or in combination with solubilized drug. Further manipulation of drug delivery, onset and profiles can be achieved by varying the concentrations of the drug in the drug carrier.

Further embodiments of the invention include those described in the detailed description.

DETAILED DESCRIPTION OF THE PREFERRED EMBODIMENTS

The foregoing and other objects are achieved by this invention which provides a transdermal drug delivery system to provide an adhesive matrix composition which effectively delivers drugs to a user over an extended period of time.

Unless defined otherwise, all technical and scientific terms used herein have the same meaning as commonly understood by one of ordinary skill in the art to which the invention pertains.

As used herein, the terms "blend" is used herein to mean that there is no, or substantially no, chemical reaction or crosslinking (other than simple H-bonding) between the different polymers in the polymer matrix. However, crosslinking between a single polymer component is fully contemplated to be within the scope of the present invention.

As used herein, the term "pressure-sensitive adhesive" refers to a viscoelastic material which adheres almost instantaneously to most substrates with the application of very slight pressure and remains permanently tacky. A polymer is a pressure-sensitive adhesive within the meaning of the term as used herein if it has the properties of a pressure-sensitive adhesive per se or functions as a pressure-sensitive adhesive by admixture with tackifiers, plasticizers or other additives. The term pressure-sensitive adhesive also includes mixtures of different polymers and mixtures of polymers, such as polyisobutylenes (PIB) of different molecular weights, the resultant mixtures being a pressure-sensitive adhesive. In the last case, the polymers of lower molecular weight in the mixture are not considered to be "tackifiers," the term "tackifier" being reserved for additives which differ other than in molecular weight from the polymers to which they are added.

The term "topical" or "topically" is used herein in its conventional meaning as referring to direct contact with an anatomical site or surface area on a mammal including skin, teeth, nails and mucosa.

The term "mucosa" as used herein means any moist anatomical membrane or surface on a mammal such as oral, buccal, vaginal, rectal, nasal or ophthalmic surfaces.

The term "transdermal" as used herein means passage into and/or through skin or mucosa for localized or systemic delivery of an active agent.

The term "solubilized" is intended to mean that in the carrier composition there is an intimate dispersion or dissolution of the active agent at the crystalline, molecular or ionic level. As such, the solublized active agent is considered herein to be in "non-crystallized" form when in the compositions of the present invention.

As used herein "flux" is defined as the percutaneous absorption of drugs through the skirt, and is described by Fick's first law of diffusion:

$$J = D(dC_m/dx),$$

where J is the flux in $g/cm^2/sec$, D is the diffusion coefficient of the drug through the skin in $cm^2/sec$ and $dC_m/dx$ is the concentration gradient of the active agent across the skin or mucosa.

The phrase "pharmaceutically acceptable flexible, finite" is intended to mean a solid form capable of conforming to a surface to which it is applied, and which is capable of maintaining the contact in such solid form so as to facilitate topical application without adverse physiological response, and without being appreciably decomposed by aqueous contact during use by a subject.

The term "user" or "subject" is intended to include all warm-blooded mammals, preferably humans.

The phrase "substantially zero-order" as used herein means transdermal delivery of an active agent at a release rate which is approximately constant once steady state is attained, typically within 12 to 24 hours after topical application. While variability in blood levels of active agent are contemplated within the scope of this meaning once steady state release is attained, the depletion rate of active agent over the duration of use should typically not exceed about 20% to about 25%.

The term "active agent" (and its equivalents "agent," "drug," "medicament" and "pharmaceutical") is intended to have the broadest meaning and includes at least one of any therapeutic, prophylactic, pharmacological or physiological active substance, cosmetic and personal care preparations, and mixtures thereof, which is delivered to a mammal to produce a desired, usually beneficial, effect. More specifically, any active agent that is capable of producing a pharmacological response, localized or systemic, irrespective of whether therapeutic, diagnostic, cosmetic or prophylactic in nature, is within the contemplation of the invention. Also within the invention are such bioactive agents as pesticides, insect repellents, sun screens, cosmetic agents, etc. It should be noted that the drugs and/or bioactive agents may be used singularly or as a mixture of two or more such agents, and in amounts sufficient to prevent, cure, diagnose or treat a disease or other condition, as the case may be. In the case of drugs, the drug can be in its free base or acid form, or in the form of salts, esters, amides, prodrugs, enantiomers or mixtures thereof, or any other pharmacologically acceptable derivatives, or as components of molecular complexes The drug is used in a "pharmacologically effective amount." This term means that the concentration of the drug is such that in the composition it results in a therapeutic level of drug delivered over the term that the transdermal dosage form is to be used, preferably with zero order kinetics. Such delivery is dependent on a great number of variables including the drug, the time period for which the individual dosage unit is to be used, the flux rate of the drug from the system and a number of other variables. The amount of drug needed can be experimentally determined based on the flux rate of the drug through the system and through the skin when used with and without enhancers. Having determined the flux rate needed, the transdermal delivery system is designed so that the release rate over the period of time of therapeutic use will be at least equal to the flux rate. Of course, the surface area of the transdermal delivery system also affects the delivery of the drug from the system.

Drugs in general can be used in this invention. These drugs include those categories and species of drugs set forth on page ther-5 to ther-29 of the Merck Index, 11th Edition Merck & Co. Rahway, N.J. (1989). Preferred drugs and pro-drugs are those that have some solubility in water and oil according to their octanol-water partition coefficient, a physical property used extensively to describe a compound's lipophilic or hydrophobic properties. The logarithm log P is commonly used to characterize its value. Such preferred drugs or pro-drugs have log P values from about 0 to about 4, more preferably from about 0 to about 3, and most preferably from about 0 to about 2.5, as calculated using EPA Software KOW-WIN version 1.67.

Particularly preferred drugs include oxymorphone, caffeine, zidovudine, pilocarpine, ranitidine, lazabemide, thiopental, scopolamine, butabarbital, digoxin, tiapride, pemoline, diclofenac, antipyrine, albuterol, oxycodone, terbutaline, ephedrine, pseudoephedrine, morphine, captopril, mescaline, naloxone, phenelzine, secobarbital, flumazenil, fluvastatin; sumatriptan, oxcarbazepine, modafinil, moclobemide, nadolol, aldosterone, pentaerythritol, prazosin, ramipril, guanfacine, physostigmine, phenobarbital, minoxidil, aprobarbital, naltrexone, leflunomide, terazosin, pindolol, fludrocortisone, mephobarbital, profentofylline, methysergide, transylcypromine, prednisone, hydromorphone, dantrolene, hydrocortisone, talipexole, lidocaine, metoprolol, betamethasone, timolol, lesopitron, benzocaine, clobazam, colchicine, butalbital, prilocalne, atropine, mepivacaine, procaine, pentobarbital, amobarbital, clorazepate, yohimbine, temazepam, hydrocodone, phenyloin, trimethobenzamide, warfarin, carbamazepam, nedociomil, buspirone, ketorolac, oxazepam, piribedil, pramipexole, secobarbital, hydrocortisone, lorazepam, chlordiazepoxide, quetiapine, enalapril, betamethasone acetate, tamsulosin, nifedipine, ergotamine, clonazepam, atorvastatin, tolmetin, bumetanide, piroxicam, perindopril, propranolol, mexiletene, chlorzoxazone, indapamide, diazepam, ciciopirox, ramipril, amphetamine, benztropine, methylphenidate, apomorphine, diltiazem, alprenolol, clozapine, ropivacaine, valproic acid, norethindrone, ketoprofen, tramadol, tetracaine, etorphine, flurazepam, meperidine, ropinirole, carvedilol, bupranolol, pravastatin, naproxen, diphenhydramine, ketamine, albendazole, idebenone, tacrine, finasteride, nabumetone, gestodene, testosterone, venlafaxine, estazolam, rimantadine, phentolamine, propafenone, levorphanol, bupivicaine, perindopril, droperidol, celecoxib, norgestrel, isradipine, risperidone, benazepril, loratidine, betamethasone, progesterone, butorphanol, papaverine, quinapril, alprostadil, prostaglandin, citalopram, ibuprofen, flurbiprofen, chlorpheniramine, zolpidem, alprazolam, fentanyl, nisoldipine, benztropine, betamethasone, etodolac, tibolone, estradiol, adamantane, chlormadinine, oxybutynin, triazolam, doxepin, prazepam, capsaicin, granisetron, frovatriptan and norethindrone acetate.

The drugs and mixtures thereof can be present in the composition in different forms, depending on which form yields the optimum delivery characteristics. Thus, in the case of drugs, the drug can be in its free base or acid form, or in the form of salts, esters, or any other pharmacologically acceptable derivatives, or as components of molecular complexes.

The amount of drug to be incorporated in the composition varies depending on the particular drug, the desired therapeutic effect, and the time span for which the device is to provide therapy. For most drugs, the passage of the drugs through the skin will be the rate-limiting step in delivery. Thus, the amount of drug and the rate of release is typically selected so as to provide transdermal delivery characterized by a zero order time dependency for a prolonged period of time. The minimum amount of drug in the system is selected based on the amount of drug which passes through the skin in the time span for which the device is to provide therapy. Normally, the amount of drug in the system can vary from about 0.01% to about 50%. However, the composition of this invention is particularly useful for drugs which are used in relatively low concentrations, especially 0.1% to 30% of the total composition, more preferably from about 0.5% to about 15% of the total composition, most preferably from about 1% to about 10% of the total composition. For certain drugs, like frovatriptan, the preferred concentration is in the range of about 15% to about 20% by weight of the total composition.

Particularly preferred drugs include scopolamine, estradiol, granisetron, frovatriptan and clonidine. Clonidine is an anti-sympathicotonic agent having an imidazoline structure. It has affinity for $\alpha_1$-adrenoceptors and—more strongly—for pre- and post-synaptic $\alpha_2$-adrenoceptors and lowers peripheral sympathetic tone. It is believed that clonidine lowers blood pressure by decreasing cardiac output and—in the case of prolonged medication—by reducing peripheral vascular resistance. At the same time, it is believed that clonidine reduces the release of renin with a decrease in angiotensin II in the blood plasma, with aldosterone being released from the adrenal cortex.

Clonidine may be used, for example, in treating the following indications: hypertension, migraine, anxiety states, hyperkinetic behavioural disorders, withdrawal symptoms in alcohol or drug withdrawal, and menopausal symptoms.

Clonidine hydrochloride exists in the form of a mesomeric component. The chemical name is 2-(2,6-dichlorophenylamino)-2-imidazoline hydrochloride. Clonidine has the following molecular formula: $C_9H_9Cl_2N_3HCl$, and a molecular weight of 266.56.

In transdermal drug delivery systems, the presence of crystals (drugs or other additives or both) is generally undesirable. Typically, if the drug is present in crystalline form, it is not available for release from the system, and therefore not available for delivery. Moreover, although drug crystals can first dissolve and then release from the system, such a process is usually rate limiting and tends to reduce transdermal permeation rates or provide non-controlled delivery rates or profiles.

In the present invention, the drug is incorporated or dispersed in crystalline form in the transdermal system carrier composition. The crystalline form used comprises two sizes—small and larger crystals—and may be present singularly or in combination depending on the desired flux and delivery rates and profiles. Optionally, an amount of the drug can also be present in non-crystalline or solubilized form where short and/or quick drug onset is also desired. Accordingly, the drug may be wholly insoluble in the carrier or adhesive composition, or partially soluble.

As used herein, the term "small crystal size" is intended to refer to a drug which is present in the transdermal drug delivery system in a particle size of from about 1 µm to about 200 µm and more preferably from about 10 µm to about 200 µm.

The term "larger crystal size" is intended to refer to a drug which is present in the transdermal drug delivery system in a particle size which is greater than the small crystal size. In other words, for example, where a first crystal size of 75 µm is used, the larger crystal size may be 100 µm. When used in conjunction with solubilized drug or alone, particularly to achieve prolonged or extended delivery, examples of larger crystal size are from about 100 µm to about 2000 µm, and more preferably from about 100 µm to about 1000 µm.

In general, therapeutic amounts of drug can be delivered from the transdermal drug delivery system containing about 0.1% to about 50% by weight of drug. However, the transdermal drug delivery system of this invention is particularly useful for drugs which are used in relatively low concentrations, especially from about 0.3% to about 30% of the total transdermal drug delivery system, more preferably from about 0.5% to about 20% of the total transdermal drug delivery system, most preferably from about 1% to about 15% of the total transdermal drug delivery system.

As set forth above, the drug may be present in the same transdermal drug delivery system in three different forms—solubilized in the transdermal drug delivery system, in small crystal size and in larger crystal size. The solubilized drug is present in the transdermal drug delivery system in an amount of from about 0.1% to about 50% by weight of the total drug amount, the small crystal size drug is present in an amount of from about 1% to about 60% by weight of the total drug amount, and the larger crystal size drug is present in an amount of from about 2% to about 70% by weight of the total drug amount.

The desired ratio of small crystal size drug to larger crystal size drug is generally from about 2:1.

The invention resulted from the discovery that the transdermal permeation rate of a drug from a carrier composition can be selectively modulated by adjusting the drug crystal size and distribution rather than exclusively the solubility of the drug in the system, in order to achieve maximum delivery of drug. As used herein, the term "transdermal permeation rate" means the rate of passage of the drug through the skin; which, as known in the art, may or may not be affected by the rate of release of the drug from the carrier.

In addition to selecting the crystal size of the drug where the presence of solubilized drug is also desired, the selection of the polymeric or adhesive carrier is equally important in order to advantageously provide a selectable modulation of the delivery rate of the drug and requiring adjusting the net solubility of the drug in the carrier composition.

Solubility parameter, also referred to herein as "SP," has been defined as the sum of all the intermolecular attractive forces, which are empirically related to the extent of mutual solubility of many chemical species. A general discussion of solubility parameters is found in an article by Vaughan, "Using Solubility Parameters in Cosmetics Formulation," *J. Soc. Cosmet. Chem.*, Vol. 36, pages 319-333 (1985).

The active agent in crystalline form or both crystalline and dissolved form is dispersed or dispersed and solubilized in a carrier. The term "carrier" as used herein refers to any non-aqueous material known in the art as suitable for transdermal drug delivery administration, and includes any material into which an active agent may be dispersed and/or solubilized in combination or admixture with the other ingredients of the composition.

The polymeric materials preferably comprise adhesives and, in particular, pressure-sensitive adhesives. An "adhesive" as used herein means any natural or synthetic material that is capable of sticking to the site of topical application. The term "pressure-sensitive adhesive" as used herein refers to an adhesive which adheres instantaneously to most surfaces with the application of very slight pressure and remains permanently tacky. An adhesive is a pressure-sensitive adhesive within the meaning of that term as used herein if it has the properties of an adhesive pressure-sensitive adhesive per se or functions as the same by admixture with tackifiers, plasticizers, cross-linking agents or other additives.

The carrier material is typically used in an amount of about 20% to about 98%, and preferably from about 30% to about 95%, and most preferably about 40% to about 95% by weight based on the dry weight of the total carrier composition. The term "carrier composition" may also refer to enhancers, solvents, co-solvents and other types of addictives useful for facilitating transdermal drug delivery.

Suitable carrier materials include all of the non-toxic natural and synthetic polymers known for or suitable for use in transdermal systems, such as solvent-based, hot melt and grafted adhesives, and may be used alone or in combinations, mixtures or blends. Examples include acrylic polymers, gums, silicone-based polymers (broadly referred to as "polysiloxanes" and including silicone fluids) and rubber-based polymers that include hydrocarbon polymers such as natural and synthetic polyisoprene; polybutylene; polyisobutylene; styrene based polymers; styrene block copolymers; butadiene based polymers; styrene/butadiene polymers; styrene-isoprene-styrene block copolymers; hydrocarbon polymers such as, for example, butyl rubber; halogen-containing polymers such as, for example, polyacrylonitrile, polytetrafluoroethylene, polyvinylchloride, polyvinylidene chloride, and polychlorodieneas polyisobutylenes, polybutylenes, ethylene/vinyl acetate and vinyl acetate based adhesives, styrene/butadiene adhesives, polyisoprenes, styrenes and styrene block copolymers and block amide copolymers, and bioadhesives set forth in U.S. Pat. No. 6,562,363 which is expressly incorporated by reference in its entirety.

Suitable polysiloxanes include silicone pressure-sensitive adhesives which are based on two major components: a polymer, or gum, and a tackifying resin. The polysiloxane adhesive is usually prepared by cross-linking the gum, typically a high molecular weight polydiorganosiloxane, with the resin, to produce a three-dimensional silicate structure, via a condensation reaction in an appropriate organic solvent. The ratio of resin to polymer is the most important factor which can be adjusted in order to modify the physical properties of polysiloxane adhesives. Sobieski, et al., "Silicone Pressure Sensitive Adhesives," Handbook of Pressure-Sensitive Adhesive Technology, 2nd ed., pp. 508-517 (D. Satas, ed.), Van Nostrand Reinhold, N.Y. (1989). Use of capped (or amine-compatible) polysiloxanes are often preferred to increase drug stability and reduce degradation.

Further details and examples of silicone pressure-sensitive adhesives which are useful in the practice of this invention are described in the following U.S. Pat. Nos. 4,591,622; 4,584, 355; 4,585,836; and 4,655,767. Suitable silicone pressure-sensitive adhesives are commercially available and include the silicone adhesives sold under the trademarks BIO-PSA® by Dow Corning Corporation, Medical Products, Midland, Mich.

In particularly preferred embodiments of the invention, the carrier matrix composition comprises a pressure-sensitive adhesive, and more preferably a blend of one or more acrylic, polysiloxane and/or rubber-based polymers, particularly polyisobutylene.

The term "acrylic polymer" is intended to be used interchangeably with the terms acrylate polymer, polyacrylate and polyacrylic adhesive polymers as used herein and as known in the art.

The acrylic polymers useful in practicing the invention are polymers of one or more monomers of acrylic acids and other copolymerizable monomers. The acrylic polymers also include copolymers of alkyl acrylates and/or methacrylates and/or copolymerizable secondary monomers or monomers with functional groups, thus providing either non-functional/reactive or functional/reactive acrylic-based polymers. By varying the amount of each type of monomer added, the cohesive properties of the resulting acrylic polymer and/or the resulting acrylic polymer's effect on drug stability can be changed as is known in the art. In general, the acrylic polymer is composed of at least 50% by weight of an acrylate or alkyl acrylate monomer, from 0 to 20% of a functional monomer copolymerizable with the acrylate, and from 0 to 40% of other monomers.

Acrylate monomers which can be used include acrylic acid, methacrylic acid, butyl acrylate, methacrylate, methyl methacrylate, butyl methacrylate, hexyl acrylate, hexyl methacrylate, 2-ethylbutyl acrylate, 2-ethylbutyl acrylate, 2-ethylbutyl methacrylate, isooctyl acrylate, isooctyl methacrylate, 2-ethylhexyl acrylate, 2-ethylhexyl methacrylate, decyl acrylate, decyl methacrylate, dodecyl acrylate, dodecyl methacrylate, tridecyl acrylate, and tridecyl methacrylate.

Functional monomers, copolymerizable with the above alkyl acrylates or methacrylates, which can be used include acrylic acid, methacrylic acid, maleic acid, maleic anhydride, hydroxyethyl acrylate, hydroxypropyl acrylate, acrylamide, dimethylacrylamide, acrylonitrile, dimethylaminoethyl acrylate, dimethylaminoethyl methacrylate, tert-butylaminoethyl acrylate, tert-butylaminoethyl methacrylate, methoxyethyl acrylate and methoxyethyl methacrylate and other monomers having at least one unsaturated double bond which participates in copolymerization reaction in one molecule and a functional group on its side chain such as a carboxyl group, a hydroxyl group, a sulfoxyl group, an amino group, an amino group and an alkoxyl, as well as a variety of other monmeric units including alkylene, hydroxy-substituted alkylene, carboxylic acid-substituted alkylene, vynylalkanoate, vynylpyrrolidone, vinylpyridine, vinylpirazine, vinylpyrrole, vinylimidazole, vinylcaprolactam, vinyloxazole, vyinlacate, vinylpropionate and vinylmorpholine.

Further details and examples of acrylic adhesives which are suitable in the practice of the invention are described in Satas, "Acrylic Adhesives," Handbook of Pressure-Sensitive Adhesive Technology, 2.sup.nd ed., pp. 396-456 (D. Satas, ed.), Van Nostrand Reinhold, N.Y. (1989).

Suitable acrylic adhesives are commercially available and include the polyacrylate adhesives sold under the trademarks DURO-TAK.® by National Starch Company, Bridgewater, N.J.; GELVA® by Cytec Surface Specialties, St. Louis, Mo.; and EUDRAGIT® by Roehm Pharma GmbH, Darmstadt, Federal Republic of Germany.

In the practice of preferred embodiments of the invention, the rubber based polymer, acrylic based polymer or polysiloxane polymer, or mixtures thereof constitutes from about 5% to about 97% of the total weight of the composition, preferably about 12% to about 97%, and more preferably from about 14% to about 94%, and most preferably from about 18 to 90% of the total weight of the carrier material. The choice of the specific polymers for the pressure sensitive adhesive composition is dependent on the type of drug used in the transdermal drug delivery system.

The rubber-based pressure sensitive adhesive can be blended with a polydiorganosiloxane polymer. By "polydiorganosiloxane polymer" is meant a silicone fluid polymer having repeat units of the formula $R_2SiO_{2/2}$ siloxy units where R is a hydrocarbon or substituted hydrocarbon having from about 1 to 20 carbons atoms and is represented by the formula:

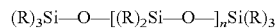

$(R)_3Si-O-[(R)_2Si-O-]_nSi(R)_3$ where R can be a hydrocarbon or substituted hydrocarbon of 1 to about 20 carbon atoms and can be selected from the group consisting of alkyl, aryl, cycloalkyl and the like which may be substituted to contain halogen, amino, hydroxy, ether or other similar functionalities. The integer "n" is sufficient to cause the silicone fluid to have a viscosity of between about 20 and 25,000 centistokes. Preferably the viscosity will be between about 20 and 12,500 centistokes. The term "polydiorganosiloxane polymer" and silicone fluid polymer are used interchangeably herein.

With reference to the above formula, preferably R is methyl and the diorganopolysiloxane is a dimethylpolysiloxane polymer generically known as dimethicone. Therefore the terms "polydimethylsiloxane" and "dimethicone" are used interchangeably and refer to the preferred diorganopolysiloxane polymer.

Polydiorganosiloxane polymer fluids may be generally classified as unmodified silicones, linear and cyclic volatile silicones, alkyl/alkoxy modified silicones, phenyl modified silicones, aminofunctionalized silicones, polyglucoside silicones and polyether functionalized silicones.

Exemplary of unmodified silicone fluid polymers suitable for use in the present invention are Dimethicone and Dimethiconol available as SP 96® (20, 50-1000), Visasil® (5M-100M) and SF18(350) from Costec Inc. (Palatine, Ill.), Dow Corning® 200 and 225 fluids from Dow Corning Corporation (Midland, Mich.), DM 100-1000, AK 5-1MM, X-345 and F-1006 from Wacker Silicones Corporation (Adrian, Mich.) and Sentry Dimethicone NF from Whitco Corporation (Greenwich, Conn.).

Representative examples of linear and cyclic volatile silicones suitable for use in the present invention are Cyclomethicone (>4) available as SF 1173, SF 1202 and SF 1204 from Costec Inc., Dow Corning® 244, 145, 344 and 345 fluids from Dow Corning Corporation and CM 040 from Wacker Silicone Corporation; Dimethicone SF96® (5) from Costec Inc. and Wacker-Besil DM 1 plus from Wacker Silicones Corporation; and Hexamethyldisiloxane available as Wacker-Besil DM 0.65 from Wacker Silicones Corporation.

Examples of alkyl/alkoxy modified silicones suitable for use in the present invention include lauryl dimethicone available as Dow Corning® Q2-5200 from Dow Corning Corp., LDM 3107VP from Wacker Silicones Corp.; Cetyl dimethicone available as Dow Corning® 2502 from Dow Corning Corp. and DMC 3071 from Wacker Silicones Corp.; Stearyl dimethicone available as SF1632 from Costec, Inc., Dow Corning® 2504 from Dow Corning Corp., and E32 from Wacker Silicones Corporation.

Illustrative of phenyl modified silicones suitable for use in the present invention are Phenyltrimeticone which as available as SF 1550 from Costec Inc., Dow Corning® 556 fluid from Dow Corning Corporation and PDM 20, 100, 1000 from Wacker Silicones Corporation.

Amino-functionalized silicones suitable for use in the present invention include, for example, Amodimethicone available as SM2658 from Costec, Inc., Dow Corning® 929 and 939 from Dow Corning Corp. and L650, 652 and ADM 6057E from Wacker Silicones Corporation; Trimethylsilylamodimethicone available as SF1708-D1, SM2101 and SM2115-D2 from Costec, Inc. Dow Corning® Q2-7224 and Q2-8220 from Dow Corning Corp. and L653, 655, 656 and ADM 3047E from Wacker Silicones Corporation.

Examples of the class of silicone polyglucosides suitable for use in the present invention is Octyl Dimethicone Ethoxy Glucoside (SPG 128) from Wacker Silicones Corporation.

Examples of polyether functionalized silicones suitable for use in the present invention include Dimethicone Copolyol available as SF 1188 from Costec, Inc. Dow Corning® 2501, 3225C, Q2-5324 and Q2-5434 from Down Corning Corp. and DMC 6032 and Cetyl Dimethicone Copolyol available as CMC 3071 from Wacker Silicones Corporation.

The above are representative and it should be understood that any polydiorganosiloxane polymer fluid functional for use in adjusting the adhesive properties of a pressure-sensitive adhesive may be utilized.

The amount of silicone fluid polymer in the pressure-sensitive adhesive may vary over a wide range as long as it effectively regulates or controls the degree of tackiness such that the adhesive retains the transdermal device on the skin of a subject for the desired period of time and yet allows for the efficient removal of the device with no or minimal skin irritation or damage. Preferred amounts of silicone fluid polymer are from about 0.5 to about 25% of the total weight of the pressure sensitive adhesive composition, preferably from about 2 to about 10% of the total weight of the pressure sensitive adhesive composition, more preferably from about 5 to about 8.5% of the total weight of the pressure sensitive adhesive composition, and most preferably about 6.5% of the total weight of the pressure sensitive adhesive composition.

The weight per unit area of the dried contact adhesive layer (matrix) is usually in the range of from about 1 mg/cm$^2$ to about 20 mg/cm$^2$, and more preferably in the range of from about 2.5 mg/cm$^2$ to about 15 mg/cm$^2$. The delivery rate is in the range of from about 0.01 mg to about 100 mg of active agent per day, and more preferably in the range of from about 0.1 mg to about 50 mg per day. Generally, the amount of drug is that sufficient to deliver a therapeutically effective amount of the active agent at a substantially zero-order kinetic rate of delivery for an extended period of time of at least three days and up to seven days or longer.

While not wishing to be bound by theory, it is believed that after application of the transdermal drug delivery device to the skin or mucosa of the user, any drug present in solubilized form in the carrier is transdermally delivered, typically at first order kinetics, faster than the small crystal size drug which is subsequently solublized in and from the moisture of the user's skin or mucosa to next deliver a second amount of drug transdermally across the skin or mucosa of the user. Finally, the larger crystal size drug in the carrier is transdermally delivered across the skin or mucosa of the user providing extended or prolonged therapy. As an example, for a seven day transdermal delivery device, the drug is delivered as set forth below:

| Drug Form Type | Drug Delivery Time (Hours) |
| --- | --- |
| Solubilized Drug | 0-40 |
| Small Crystal Drug | 6-85 |
| Larger Crystal Drug | 65-168 |

As is understood by the person having ordinary skill in this art, by tailoring the type of drug, the makeup of the carrier composition, the crystalline size(s) of the drug, the amount of drug, the ratio of the small and larger crystal drug size, and the amount of solubilized drug in the carrier composition and, optionally, even encapsulating the drug crystals, the transdermal drug delivery device can be tailored to deliver drug to a user over a prolonged period of topical administration, i.e., up to 7 days or longer.

Those skilled in the art can readily determine the rate of delivery of drugs from the carrier composition in order to select suitable combination(s) of polymers and drug for a particular application. Various techniques can be used to determine the rate of delivery of the drug from the carrier. Illustratively, the rate of delivery can be determined by measuring the transfer of drug from one chamber to another through cadaver skin over time, and calculating, from the obtained data, the drug delivery or flux rate.

Of course, the carrier composition of the transdermal drug delivery system can also contain agents known to accelerate the delivery of the drug through the skin. These agents have been referred to as skin penetration enhancers, accelerants, adjuvants, and sorption promoters, and are collectively referred to herein as "enhancers." This class of agents includes those with diverse mechanisms of action including those which have the function of improving the solubility and diffusibility of the drug within the multiple polymer and those which improve percutaneous absorption, for example, by changing the ability of the stratum corneum to retain moisture, softening the skin, improving the skin's permeability, acting as penetration assistants or hair-follicle openers or changing the state of the skin including the boundary layer. Some of these agents have more than one mechanism of action, but in essence they serve to enhance the delivery of the drug. An enhancer may be included in a drug delivery system up then the enhancer is preferably present in an amount of about 1% to about 10% by weight. Some examples of enhancers are polyhydric alcohols such as dipropylene glycol, propylene glycol, and polyethylene glycol which enhance drug solubility; oils such as olive oil, squalene, and lanolin; polyethylene glycol ethers and fatty ethers such as cetyl ether and oleyl ether; fatty acid esters such as isopropyl myristate which enhance drug diffusibility; fatty acid alcohols such as oleyl alcohol; urea and urea derivatives such as allantoin which affect the ability of keratin to retain moisture; polar solvents such as dimethyldecylphosphoxide, methyloctylsulfoxide, dimethyllaurylamide, dodecylpyrrolidone, isosorbitol, dimethylacetonide, dimethylsulfoxide, decylmethylsulfoxide, and dimethylformamide which affect keratin permeability;

salicylic acid which softens the keratin; amino acids which are penetration assistants; benzyl nicotinate which is a hair follicle opener; and higher molecular weight aliphatic surfactants such as lauryl sulfate salts which change the surface state of the skin and drugs administered. Other agents include oleic and linoleic acids, ascorbic acid, panthenol, butylated hydroxytoluene, tocopherol, tocopheryl acetate, tocopheryl linoleate, propyl oleate, isopropyl palmitate, oleamide, polyoxyethylene (4) lauryl ether, polyoxyethylene (2) oleyl ether and polyoxyethylene (10) oleyl ether sold under the trademarks Brij 30, 93 and 97 by ICI Americas, Inc., and polysorbate 20 sold under the trademark Tween 20 by Id Americas, Inc.

In certain embodiments of the invention a plasticizer or tackifying agent is incorporated into the formulation to improve the adhesive characteristics of the pressure-sensitive adhesive composition. A tackifying agent is particularly useful in those embodiments in which the drug does not plasticize the polymer. Suitable tackifying agents are those known in the art including: (1) aliphatic hydrocarbons; (2) mixed aliphatic and aromatic hydrocarbons; (3) aromatic hydrocarbons; (4) substituted aromatic hydrocarbons; (5) hydrogenated esters; (6) polyterpenes; and (7) hydrogenated wood resins or rosins. The tackifying agent employed is preferably compatible with the blend of polymers. In preferred embodiments, the tackifying agent is silicone fluid (e.g., 360 Medical Fluid, available from Dow Corning Corporation, Midland, Mich.) or mineral oil. Silicone fluid is useful for blends comprising polysiloxane as a major component. In other embodiments, where a synthetic rubber, for example, is a major component, mineral oil is a preferred tackifying agent. Acrylics can be tackified with oleates, oleic acid, oleyl alcohol and other fatty acid-derived agents.

For drug molecules which are not readily soluble in the carrier polymer system, a co-solvent for the drug and polymer can be added. Co-solvents, such as lecithin, retinol derivatives, tocopherol, dipropylene glycol, triacetin, propylene glycol, saturated and unsaturated fatty acids, mineral oil, silicone fluid, alcohols, butyl benzyl phthalate, and the like are useful in the practice of the instant invention depending on the net solubility of the drug in the carrier composition.

The compositions of this invention may further be provided with various thickeners, fillers and other additives known for use with transdermal drug delivery systems.

In a device aspect of the invention, the pressure-sensitive adhesive composition can be used as an adhesive portion of any transdermal drug delivery system (e.g., a reservoir device) or it can comprise an adhesive monolithic. Of course, the principles of the invention would still apply to embodiments where the transdermal drug delivery composition is not a pressure-sensitive adhesive and comprises a drug reservoir.

A device, or individual dosage unit, of the present invention can be produced in any manner known to those of skill in the art. After the dermal composition is formed, it may be brought into contact with an occlusive backing layer in any manner known to those of skill in the art. Such techniques include calendar coating, hot melt coating, solution coating, etc. Of course, occlusive backing materials are well known in the art and can comprise plastic films of polyethylene, vinyl acetate resins, polyester, polypropylene, BAREX®, ethylene/vinyl acetate copolymers, polyvinyl chloride, polyurethane, and the like, metal foils, non-woven fabric, cloth, coextrusions or laminations of the above and commercially available laminates. The occlusive backing material generally has a thickness in the range of 2 to 1000 micrometers and the dermal composition is generally disposed on backing material in a thickness ranging from about 12 to 250 micrometers thick.

Suitable release liners are also well known in the art and include the commercially available products of Release International designated Bio-Release® liner and Syl-off® 7610 liner. For preferred embodiments in which a polysiloxane is part of the multiple polymer adhesive system, the release liner must be compatible with the silicone adhesive. An example of a suitable commercially available liner is 3M's 1022 Scotch Pak®.

In a method aspect of the invention, a plurality of polymers are blended (but not chemically reacted or cross-linked) to result in a pressure-sensitive adhesive composition which controls delivery of an incorporated drug through the skin or mucosa. The term "blending," of course, incorporates choosing the appropriate polymeric components, and the proportions thereof, to achieve the desired effect.

Drug is blended with the pressure sensitive adhesives to solubilize the drug into the pressure sensitive adhesive composition. Crystallized drug is then added to the composition. Customary substances such as fillers, skin-protective substances, tackifiers or the like may be added if desired, but it is not essential. The mixture is then blended together to form a flexible, finite composition. The system is freed of solvent in a dryer located downstream. After leaving the dryer, the then dry and self-adhesive active ingredient/adhesive matrix is laminated with a further layer, which may be e.g. a plastics film, a non-woven fabric, a plastics foam, a woven fabric or the like, for covering purposes.

Suitable volatile solvents include, but are not limited to, alcohols such as isopropanol and ethanol; aromatics such as xylenes and toluene; aliphatics such as hexane, cyclohexane, and heptane; and alkanoic acid esters such as ethyl acetate and butyl acetate.

An exemplary general method for the preparation of a preferred embodiment is as follows:

1. Appropriate amounts of polysiloxane and rubber adhesives, or polymers solvent(s), enhancer(s), and organic solvent(s) (for example toluene) are combined and thoroughly mixed together in a vessel.
2. The drug is then added to the mixture and agitation is carried out until the drug is uniformly mixed.
3. Small and larger crystals of the drug are then added to the mixture and thoroughly mixed.
4. The formulation is then transferred to a coating operation where it is coated onto a protective release liner at a controlled specified thickness. The coated product is then passed through an oven in order to drive off all volatile processing solvents.
5. The dried product on the release liner is then joined to the backing material and wound into rolls for storage.
6. Appropriate size and shape "systems" are die-cut from the roll material and then pouched.

The order of steps, the amount of the ingredients, and the amount and time of agitation or mixing may be importance process variables which will depend on the specific polymers, drug, cosolvents, and enhancers used in the formulation. These factors can be adjusted by those skilled in the art, while keeping in mind the object of providing a uniform product. It is believed that a number of other methods, including changing some of the order of steps, can be carried out and will give desirable results. In addition to having various shapes, the dosage units produces may come in various sizes. A surface area in the range of 1 to 200 $cm^2$ is contemplated, and the presently preferred sizes are from about 5 to about 60 $cm^2$.

Further details and examples of pressure-sensitive adhesives, enhancers, solvents, co-solvents, release liners, backing layers, and other additives, as well as transdermal systems generally, suitable in practicing the invention are described in U.S. Pat. Nos. 5,474,787, 5,958,446, 6,024,976, 6,562,363 and 60/488,928, all of which are assigned to Noven Pharmaceuticals, Inc. and incorporated herein by reference.

The present invention is illustrated by the following examples, without limiting the scope of the invention.

EXAMPLES

Figure 2:
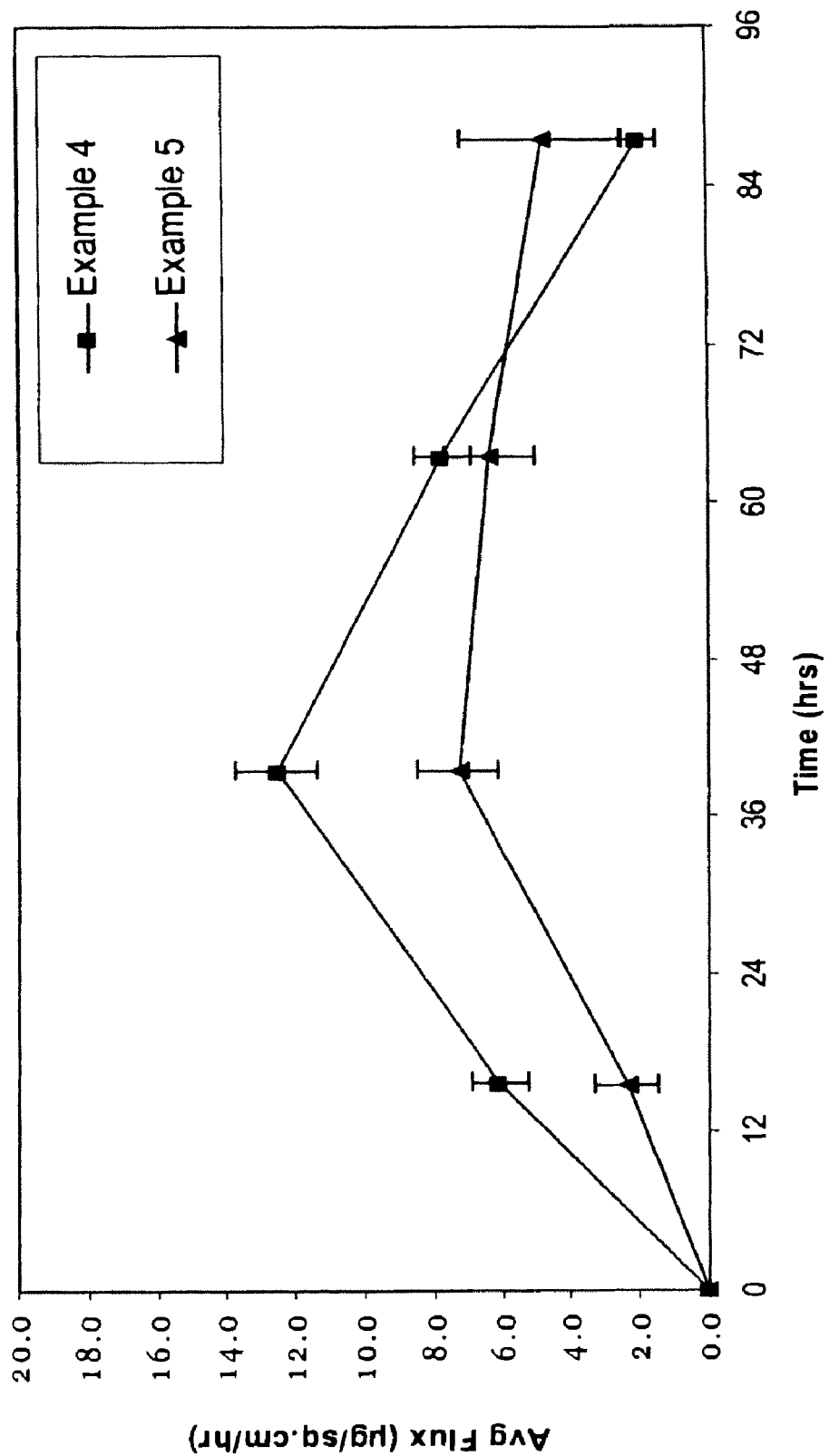
FIG. 2 is a graphic representation of the effects on drug delivery, onset and profile of frovatriptan with different crystal sizes of the drug in pressure-sensitive adhesive compositions.

In the Examples as shown with respect to FIGS. 1 and 2, the effect of variations in the crystal size of the drug are determined, indicating that by modifying the crystal size of the drug, one can effectively control permeation rate, onset and profile of the drug in the transdermal delivery system.

The carrier compositions containing clonidine and frovatriptan were prepared and coated onto a fluoropolymer release liner and dried for 5 minutes at RT and 5 minutes in a 92° C. oven to produce a pressure-sensitive adhesive (PSA) carrier composition by dry weight as set forth below.

|  | Example 1 | Example 2 | Example 3 |
|---|---|---|---|
| Silicone PSA (BIO PSA-4302) | 85 | 85 | 85 |
| Polyisobutylene (Vistanex) | 10 | 10 | 0 |
| Acrylic PSA (DURO-TAK 87-2100) | 0 | 0 | 10 |
| Clonidine | 5 | 5 | 5 |
| Crystal Size of Clonidine | 200-250 μm | 75 μm average | Dissolved |

|  | Example 4 | Example 5 |
|---|---|---|
| Silicone PSA (BIO PSA-4302) | 40 | 40 |
| Acrylic PSA (Gelva 3087) | 40 | 40 |
| Butylene Glycol | 5 | 5 |
| Oleth 3 (Brij) | 5 | 5 |
| Frovatriptan Base | 10 | 10 |
| Crystal Size of Frovatriptan Base | 1-200 μm | 200-250 μm |

Determination of drug flux of the described formulations was conducted on a modified Franz Diffusion cell through a disc of stratum corneum obtained from human cadaver skin. The transdermal systems were die-cut punched, mounted on the disc, and placed on the cell, which contained an isotonic saline solution. The cells were stored at 32° C. for the duration of each flux study while having the solution stirred at a constant rate of approximately 300 rpm. Samples (n=5) of the solution were taken at various time points over the study duration, and drug concentrations were determined by high pressure liquid chromatography.

FIG. 1 illustrates that the drug from in Example 3, being solubilized or in non-crystallized form, reaches maximum delivery within 24 hours followed by a significant decrease in flux. However, as demonstrated in Examples 1 and 2, which contain crystallized clonidine, a sustained seven-day delivery at substantially zero order is achievable as compared to the rapid release of dissolved drug in Example 3. As can be further seen from FIG. 1, the larger crystals used in Example 1 produce a lower permeation rate (flux) than the smaller crystals used in Example 2. Thus, FIG. 1 shows that crystal particle size contributes to variations in drug delivery rates.

FIG. 2 further illustrates how drug particle size can be manipulated to achieve variations in drug delivery rates/profiles.

The above description and examples are only illustrative of preferred embodiments which achieve the objects, features, and advantages of the present invention, and it is not intended that the present invention be limited thereto.

What is claimed is:

1. A transdermal drug delivery system comprising a pressure sensitive adhesive composition which comprises a blend of:
    (a) one or more polymers selected from the group consisting of a rubber based polymer, an acrylic based polymer and a polysiloxane; and
    (b) a pharmacologically effective amount at least one drug for transdermal drug delivery, wherein said at least one drug is (i) solubilized in said pressure sensitive adhesive, (ii) incorporated in said pressure sensitive adhesive in crystal form having a small crystal size, and (iii) incorporated in said pressure sensitive adhesive in crystal form having a larger crystal size,
    wherein the amount of drug solubilized in said pressure sensitive adhesive, the amount of drug incorporated in said pressure sensitive adhesive in crystal form having a small crystal size, and the amount of drug incorporated in said pressure sensitive adhesive in crystal form having a larger crystal size are selectively tailored to control the drug delivery rate and profile of the drug from the transdermal drug delivery system.

2. The transdermal drug delivery system according to claim 1, wherein the one or more polymers comprises a rubber based polymer which is present in an amount from 5% to 97% by weight of said pressure sensitive adhesive composition.

3. The transdermal drug delivery system according to claim 2, wherein said rubber based polymer is selected from the group consisting of natural and synthetic polyisoprene, polybutylene, polyisolyobutylene, styrene based polymers, styrene block copolymers, butadiene based polymer, styrene/butadiene polymers, styrene-isoprene-styrene block copolymers, hydrocarbon polymers, and halogen-containing polymers.

4. The transdermal drug delivery system according to claim 2, wherein said rubber based polymer includes polyisobutylene.

5. The transdermal drug delivery system according to claim 1, wherein said one or more polymers comprises a polysiloxanc polymer present in an amount from 5% to 97% by weight of said pressure sensitive adhesive composition.

6. The transdermal drug delivery system according to claim 1, wherein the one or more polymers comprises a silicone fluid polymer present in an amount of from about 0.5 to about 25% of the pressure sensitive adhesive composition.

7. The transdermal drug delivery system according to claim 6, wherein said silicone fluid polymer includes dimethicone.

8. The transdermal drug delivery system according to claim 1, wherein the one or more polymers comprises at least one acrylic-based polymer present in an amount from 5% to 97% by weight of said pressure sensitive adhesive composition.

9. The transdermal drug delivery system according to claim 8, wherein the acrylic-based polymer includes at least 50% by weight of an acrylate or alkyl acrylate monomer, from 0 to 20% by weight of a functional monomer copolymerizable with the acrylate or alkyl acrylate monomer, and from 0 to 40% by weight of other monomers.

10. The transdermal drug delivery system according to claim 1, wherein the drug is selected from the group consisting of scopolamine, estradiol, granisetron, frovatriptan and clonidine.

11. The transdermal drug delivery system according to claim 1, wherein the drug includes clonidine.

12. The transdermal drug delivery system according to claim 1, wherein the drug includes frovatriptan.

13. The transdermal drug delivery system according to claim 1, wherein the drug is present in said transdermal drug delivery system in an amount selected from the group consisting of (i) about 0.1% to about 50%, (ii) about 0.3% to about 30%, (iii) about 0.5% to about 15%, and (iv) about 1% to about 10%, all by weight of said pressure sensitive adhesive composition.

14. The transdermal drug delivery system according to claim 1, wherein said solubilized drug is incorporated in the transdermal drug delivery system in an amount of from 0.1 to about 50% by weight of the total drug amount.

15. The transdermal drug delivery system according to claim 1, wherein said small crystal size drug is incorporated in the transdermal drug delivery system in an amount of from 1 to about 60% by weight of the total drug amount.

16. The transdermal drug delivery system according to claim 1, wherein said larger crystal size drug is incorporated in the transdermal drug delivery system in an amount of from 2 to about 70% by weight of the total drug amount.

17. The transdermal drug delivery system according to claim 1, wherein the ratio of said small crystal size drug to said larger crystal size drug is about 2:1.

18. The transdermal drug delivery system according to claim 1, wherein said small crystal size is from about 1 μm to about 200 μm.

19. The transdermal drug delivery system according to claim 1, wherein said larger crystal size is from about 100 μm to about 2000 μm.

20. The transdermal drug delivery system according to claim 18, wherein said larger crystal size is from about 100 μm to about 2000 μm.

21. A transdermal drug delivery system comprising a pressure sensitive adhesive composition comprising a blend of:
(a) one or more polymers selected from the group consisting of a rubber based polymer, an acrylic based polymer and a polysiloxane, present in an amount from 5% to 97% by weight of said pressure sensitive adhesive composition; and
(b) a pharmacologically effective amount at least one drug for transdermal drug delivery, wherein said at least one drug is (i) solubilized in said pressure sensitive adhesive, (ii) incorporated in said pressure sensitive adhesive in crystal form having a small crystal size of from about 1 μm to about 200 μm, and (iii) incorporated in said pressure sensitive adhesive in crystal form having a larger crystal size of from about 100 μm to about 2000 μm,
wherein the amount of drug solubilized in said pressure sensitive adhesive, the amount of drug incorporated in said pressure sensitive adhesive in crystal form having a small crystal size, and the amount of drug incorporated in said pressure sensitive adhesive in crystal form having a larger crystal size are selectively tailored to control the drug delivery rate and profile of the drug from the transdermal drug delivery system.

22. A method for transdermally delivering a drug to a subject in need thereof comprising administering the transdermal drug delivery device according to claim 1 to said subject.

23. A method for transdermally delivering a drug to a subject in need thereof comprising administering the transdermal drug delivery device according to claim 21 to said subject.

* * * * *